(12) United States Patent
Ikeda et al.

(10) Patent No.: US 11,278,344 B2
(45) Date of Patent: Mar. 22, 2022

(54) POWER FEED SYSTEM

(71) Applicant: KYUSHU UNIVERSITY, NATIONAL UNIVERSITY CORPORATION, Fukuoka (JP)

(72) Inventors: Tetsuo Ikeda, Fukuoka (JP); Haruichi Kanaya, Fukuoka (JP); Ryosuke Tsutsumi, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 16/329,054

(22) PCT Filed: Aug. 31, 2017

(86) PCT No.: PCT/JP2017/031440
§ 371 (c)(1),
(2) Date: Feb. 27, 2019

(87) PCT Pub. No.: WO2018/043670
PCT Pub. Date: Mar. 8, 2018

(65) Prior Publication Data
US 2019/0216524 A1    Jul. 18, 2019

(30) Foreign Application Priority Data
Aug. 31, 2016  (JP) .............................. JP2016-170299

(51) Int. Cl.
*A61B 18/10* (2006.01)
*A61F 2/08* (2006.01)
(Continued)

(52) U.S. Cl.
CPC .............. *A61B 18/10* (2013.01); *A61B 90/00* (2016.02); *A61F 2/08* (2013.01); *A61F 17/00* (2013.01);
(Continued)

(58) Field of Classification Search
CPC .......... A61B 5/0402; A61N 1/36; A61N 2/02
(Continued)

(56) References Cited

U.S. PATENT DOCUMENTS

| | | | |
|---|---|---|---|
| 8,515,559 B2 | 8/2013 | Roberts et al. | |
| 2009/0149895 A1* | 6/2009 | Dacey, Jr. .......... | A61N 1/36071 607/3 |

(Continued)

FOREIGN PATENT DOCUMENTS

| | | |
|---|---|---|
| EP | 2 764 889 A1 | 8/2014 |
| JP | 2004-159456 A | 6/2004 |

(Continued)

OTHER PUBLICATIONS

John S. Ho et al., "Wireless power transfer to deep tissue microimplants", Proceedings of the National Academy of Sciences of the United States of America, Jun. 3, 2014, pp. 7974-7979, vol. 111, No. 22, Available at https://www.pnas.org/cgi/doi.10.1073/pnas.1403002111, National Academy of Sciences, USA.

John S. Ho et al., "Energy Transfer for Implantable Electronics in the Electromagnetic Midfield", Progress In Electromagnetics Research, Jan. 2014, pp. 151-158, vol. 148, DOI: 10.2528/PIER14070603, EMW Publishing.

(Continued)

*Primary Examiner* — Jon Eric C Morales
(74) *Attorney, Agent, or Firm* — Michael Best & Friedrich LLP

(57) ABSTRACT

[Problem] To provide a power feed system that supplies electric power via electromagnetic waves to an implant embedded in a deep part of a living body, using a sandwiching method in which a potential difference is generated using a pair of electrodes, by disposing an implant electronic device between a power transmission side electrode and a power reception side electrode.

(Continued)

[Solution] It is provided with: a pair of electrodes (a first surface electrode 3 and a second surface electrode 4) stuck onto a surface of a living body 6; an implant electronic device 2 that includes a first body internal electrode 30 and a second body internal electrode 40 and in which the first body internal electrode 30 and the second body internal electrode 40 are fixed to respective positions having different potential differences in the living body 6; and a high frequency AC power source 5 that applies a high frequency alternating voltage to the first surface electrode 3 and the second surface electrode 4.

12 Claims, 20 Drawing Sheets

(51) Int. Cl.
  *H02J 50/20* (2016.01)
  *A61B 90/00* (2016.01)
  *A61F 17/00* (2006.01)
  *A61N 1/378* (2006.01)
(52) U.S. Cl.
  CPC ........... *A61N 1/378* (2013.01); *A61N 1/3787* (2013.01); *H02J 50/20* (2016.02)
(58) Field of Classification Search
  USPC .................................................. 600/509, 13
  See application file for complete search history.

(56) References Cited

U.S. PATENT DOCUMENTS

| | | | |
|---|---|---|---|
| 2010/0016929 A1* | 1/2010 | Prochazka | A61N 1/36021 607/72 |
| 2012/0089037 A1* | 4/2012 | Bishay | A61B 5/6833 600/509 |
| 2013/0123568 A1* | 5/2013 | Hamilton | A61N 1/36017 600/13 |
| 2014/0222109 A1 | 8/2014 | Moulder | |
| 2017/0312522 A1* | 11/2017 | Kluger | A61N 1/36185 |

FOREIGN PATENT DOCUMENTS

| | | |
|---|---|---|
| JP | 2010-115025 A | 5/2010 |
| JP | 2013-055423 A | 3/2013 |

OTHER PUBLICATIONS

International Search Report issued in Application No. PCT/JP2017/031440, dated Oct. 24, 2017.
Supplementary European Search Report issued in European Application No. 17846674, dated May 20, 2020.
Office Action issued in Japanese Application No. 2018-537412, dated Apr. 27, 2021.

* cited by examiner

C1, C3:0.47μF, C2:5600pF, C4:0.1pF
LED9, LED10: 570nm

POWER SUPPLY TO CIRCUIT AND LIGHT EMISSION

CIRCUIT ENLARGEMENT

LED ONLY (CIRCUIT LENGTH 0.5 cm)

LED + SERIES RESONANCE CIRCUIT
(CIRCUIT LENGTH 2.3 cm)

LED + AMPLIFIER CIRCUIT
(COCKCROFT SINGLE-STAGE CIRCUIT)
(CIRCUIT LENGTH 1.3 cm)

LED + AMPLIFIER CIRCUIT(COCKCROFT SINGLE-STAGE CIRCUIT) + SERIES RESONANCE CIRCUIT
(CIRCUIT LENGTH 3 cm)

LED + AMPLIFIER CIRCUIT (COCKCROFT THREE-STAGE CIRCUIT)
(CIRCUIT LENGTH 2 cm)

LED + AMPLIFIER CIRCUIT (COCKCROFT THREE-STAGE CIRCUIT) + SERIES RESONANCE CIRCUIT
(CIRCUIT LENGTH 3.6 cm)

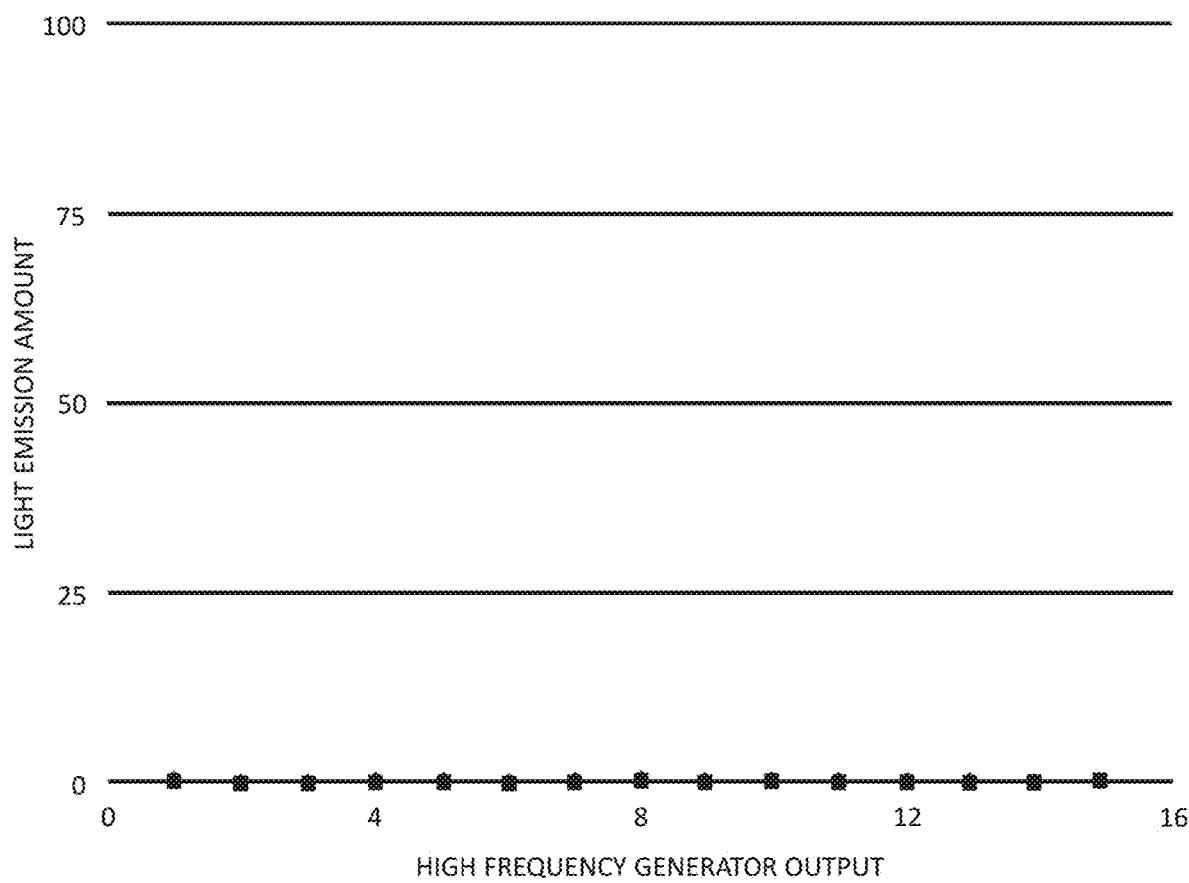

POWER FEED SYSTEM

TECHNICAL FIELD

The present invention relates to a power feed system that supplies electric power from outside of a body to an implant embedded in the body.

BACKGROUND ART

There is known a method of utilizing magnetic resonance as a method for wirelessly supplying electric power to the inside of a living body. However, this method has problems such as, for example, diffusion of energy of a radio wave oscillated from a power transmission part in every direction, and it is difficult to adapt this method to an implant embedded in the deep part of a living body. With respect to such a technology, techniques described in Non-Patent Literatures 1 and 2 (hereinafter, referred to as "NPL 1" and "NPL 2," respectively) are disclosed, for example. Hereinafter, this method is referred to as a one-side power transmission method.

CITATION LIST

Non-Patent Literature

NPL 1
John S. Ho, Alexander J. Yeh, Evgenios Neofytou, Sanghoek Kim, Yuji Tanabe, Bhagat Patlolla, Ramin E. Beygui, and Ada S. Y. Poon, "Wireless power transfer to deep-tissue microimplants," Proceedings of the National Academy of Sciences of the United States of America, vol. 111, no. 22, 7974-7979, Jun. 3, 2014

NPL 2
John S. Ho and Ada S. Y. Poon, "Energy Transfer for Implantable Electronics in the Electromagnetic Midfield," Progress In Electromagnetics Research, Vol. 148, 151-158, 2014

SUMMARY OF INVENTION

Technical Problem

However, the techniques such as those described in NPL 1 and NPL 2 require strongly coupled magnetic resonance for stable power transmission to the deep part of a living body. Further, these techniques are a bilateral power transmission system between a power transmission antenna and an implant electronic device. Therefore, these techniques have a problem that a low output power transmission wave cannot be focused and penetrate deep into the body.

The present invention provides a power feed system that supplies electric power to an implant embedded in a deep part of a living body, using a sandwiching method in which a potential difference is generated using a pair of electrodes, by disposing an implant electronic device between a power transmission side electrode and a power reception side electrode.

Solution to Problem

A power feed system according to the present invention includes: a pair of electrodes that are stuck onto a surface of a living body; an electronic device that includes a first electrode and a second electrode, the first electrode and the second electrode being fixed to respective positions having different electric potentials in the living body; and a power source that applies a high frequency alternating voltage between the pair of electrodes.

As described above, in the power feed system according to the present invention, the high frequency alternating voltage applied between the pair of electrodes makes it possible to cause a current to flow using a potential difference of a living body, resulting in an advantageous effect that it is possible to stably and sufficiently supply electric power to an electronic device attached deep within a living body to drive it by an external power supply. Further, since it does not require a battery, it results in an advantageous effect that it is possible to make the electronic device small in size.

The power feed system according to the present invention is such that the first electrode and the second electrode of the electronic device are arranged at both longitudinal ends of the electronic device.

As described above, in the power feed system according to the present invention, the first electrode and the second electrode of the electronic device are arranged at both longitudinal ends of the electronic device, so that it is possible to make the distance between the first electrode and the second electrode as long as possible, resulting in an advantageous effect that it is possible to supply a current with a large potential difference.

The power feed system according to the present invention is such that a part of the electronic device other than where the first electrode and the second electrode are fixed in the living body is insulated.

As described above, in the power feed system according to the present invention, a part of the electronic device other than where the first electrode and the second electrode are fixed in the living body is insulated, so that it results in an advantageous effect that it is possible to supply a current to the electronic device without being short-circuited even when the electronic device contacts a tissue in a living body.

The power feed system according to the present invention is such that a resistance value of the pair of electrodes is equal to or less than a ground resistance.

As described above, in the power feed system according to the present invention, a resistance value of the pair of electrodes is equal to or less than a ground resistance, so that it results in an advantageous effect that it is possible to efficiently supply a current to an electronic device fixed in a living body.

The power feed system according to the present invention is such that a resistance value of the electronic device is $\frac{1}{10}$ or less of a biological resistance.

As described above, in the power feed system according to the present invention, a resistance value of the electronic device is $\frac{1}{10}$ or less of a biological resistance, so that it results in an advantageous effect that it is possible to supply a current to the electronic device efficiently with low resistance.

The power feed system according to the present invention is such that the power source applies a high frequency signal of 100 kHz to 4 MHz.

As described above, in the power feed system according to the present invention, the power source applies a high frequency signal of 100 kHz to 4 MHz, so that it results in an advantageous effect that it is possible to supply sufficient electric power to an electronic device within a living body, using a small apparatus, without causing a thermal burn or the like.

The power feed system according to the present invention is such that the electronic device includes an amplifier circuit having at least one stage or more.

As described above, in the power feed system according to the present invention, the electronic device includes an amplifier circuit having at least one stage or more, so that it results in an advantageous effect that it is possible to amplify a current to efficiently supply the current to an electronic device fixed in a living body.

The power feed system according to the present invention further includes: a resonance circuit having at least one stage or more, which is composed of a coil and a capacitor and is configured to satisfy $f=1/(2\pi\sqrt{(LC)})$, where f is a frequency of the high frequency alternating voltage applied between the pair of electrodes, L is a self-inductance of the coil, and C is a capacitance of the capacitor; and a booster rectifier circuit having at least one stage or more, which has two capacitors and two diodes connected in a ladder shape and converts the high frequency alternating voltage into a direct voltage, wherein the number of stages of the booster rectifier circuit is determined according to the magnitude of parasitic components of the coil, the capacitor, and the diode.

As described above, in the power feed system according to the present invention, it is further provided with: a resonance circuit having at least one stage or more, which is composed of a coil and a capacitor and is configured to satisfy $f=1/(2\pi\sqrt{(LC)})$, where f is a frequency of the high frequency alternating voltage applied between the pair of electrodes, L is a self-inductance of the coil, and C is a capacitance of the capacitor; and a booster rectifier circuit having at least one stage or more, which has two capacitors and two diodes connected in a ladder shape and converts the high frequency alternating voltage into a direct voltage, and the number of stages of the booster rectifier circuit is determined according to the magnitude of parasitic components of the coil, the capacitor, and the diode, so that it results in an advantageous effect that it is possible to efficiently supply a current to an implant electronic device in a deep part of a living body by the booster rectifier circuit having the optimum number of stages.

The power feed system according to the present invention is such that the electronic device comprises a light emitting diode, a heat generating diode, a nerve stimulating device, a biometric information sensor, a cochlear implant, an artificial retina, an artificial spinal cord, an artificial anal sphincter, an artificial heart, a self-moving endoscope, and/or a micro robotic surgery.

As described above, in the power feed system according to the present invention, the electronic device comprises a light emitting diode, a heat generating diode, a nerve stimulating device, a biometric information sensor, a cochlear implant, an artificial retina, an artificial spinal cord, an artificial anal sphincter, an artificial heart, a self-moving endoscope, and/or a micro robotic surgery, so that it results in an advantageous effect that it is possible to artificially realize a necessary function(s) in a living body without using a large-scale apparatus.

The power feed system according to the present invention is such that the electronic device comprises a pair of light emitting diodes, one of the light emitting diodes emits light by a current flowing from the second electrode to the first electrode, the other light emitting diode emits light by a current flowing from the first electrode to the second electrode, and the pair of light emitting diodes are arranged respectively on a front surface side and a rear surface side of a substrate.

As described above, in the power feed system according to the present invention, the electronic device comprises a pair of light emitting diodes, one of the light emitting diodes emits light by a current flowing from the second electrode to the first electrode, the other light emitting diode emits light by a current flowing from the first electrode to the second electrode, and the pair of light emitting diodes are arranged respectively on a front surface side and a rear surface side of a substrate, so that it results in advantageous effects that it is possible to make the electronic device serve as a surgical marker and that the arrangement of the light emitting diodes serving as marks on the front and rear sides of the substrate makes it possible to prevent light emission of the light emitting diodes from being missed, obstructed by the substrate, when the inside of a body is observed with an endoscope or the like.

The power feed system according to the present invention further includes an engaging part that engages with a conductive holding member inserted into a tissue in the living body, wherein the engaging part comprises a flexible conductive metal body that is deformable by compression into an elongate shape such that the same direction as a longitudinal direction of the electronic device coincides with a longitudinal direction of the engaging part.

As described above, in the power feed system according to the present invention, it is further provided with an engaging part that engages with a conductive holding member inserted into a tissue in the living body, and the engaging part comprises a flexible conductive metal body that is deformable by compression into an elongate shape such that the same direction as a longitudinal direction of the electronic device coincides with a longitudinal direction of the engaging part, so that it is possible to carry the electronic device including electrodes at both ends thereof into the body through a forceps hole of a flexible endoscope used for endoscopic surgery or the like and to, after carrying it to a predetermined part, expand the engaging part to hold the electronic device by the holding member, resulting in an advantageous effect that it is possible to attach the electronic device within the body while minimizing the burden on a patient.

BRIEF DESCRIPTION OF DRAWINGS

FIG. 20 is a diagram showing experimental results in the case of the one-side method.

DESCRIPTION OF EMBODIMENTS

Figure 1A:
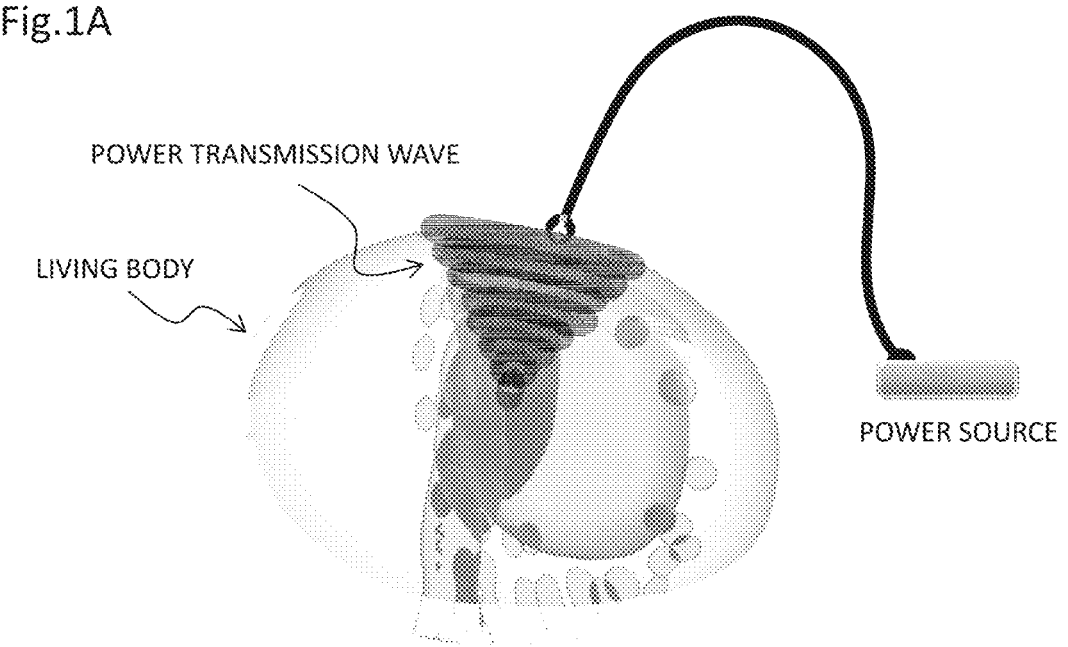
FIGS. 1A and 1B are schematic diagrams of a power feed system for each power transmission system.

Hereinafter, embodiments of the present invention will be described. In addition, the same reference numerals are given to the same elements throughout the embodiments.

First Embodiment of the Present Invention

A power feed system according to the present embodiment will be described with reference to FIGS. 1A to 3C. The power feed system according to the present embodiment is a wireless power transmission system based on a sandwiching method in which a pair of electrodes are attached to a living body and a high frequency alternating voltage is applied to generate a potential difference in the living body. In other words, it is a trilateral power transmission system in which a living body is considered as a part of an electronic circuit and an implant electronic device is disposed between a power transmission side electrode and a power reception side electrode which are alternately switched, and thereby an electromagnetic wave penetrating the living body is transmitted to the implant.

Figure 1B:
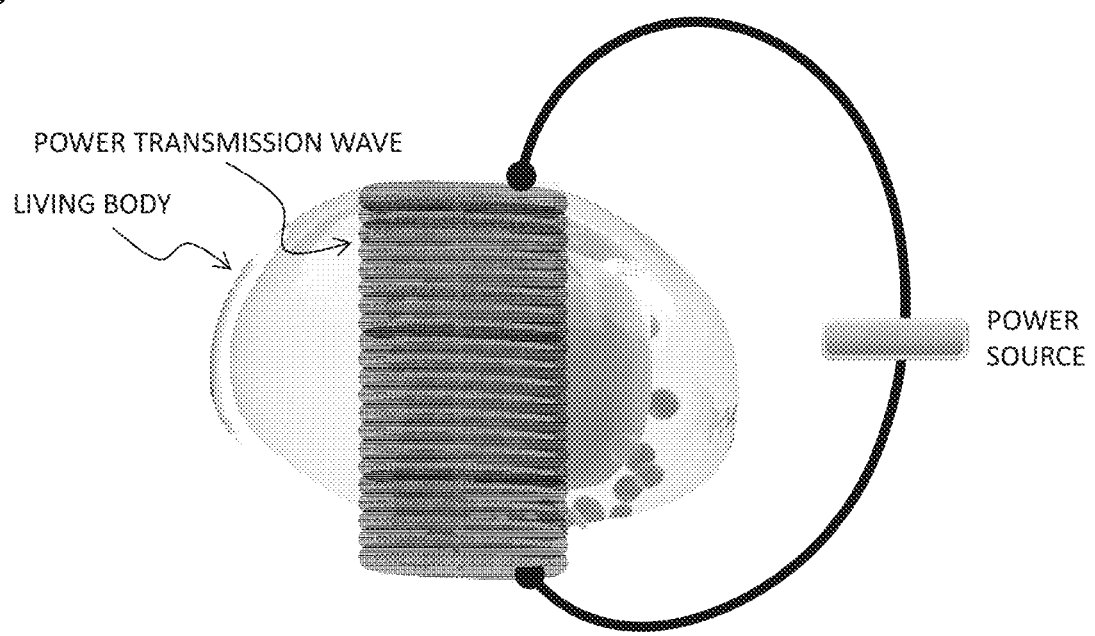

FIGS. 1A and 1B are schematic diagrams of a power feed system for each power transmission system. FIG. 1A shows a one-side power transmission system, and FIG. 1B shows a power feed system by an ungrounded type sandwiching method. In the case of the one-side power transmission system shown in FIG. 1A, a power transmission wave does not penetrate into a living body, so that it is difficult to transmit electric power to a deep part of the living body. On the other hand, in the case of the ungrounded sandwiching power transmission system, bipolar power transmission allows a power transmission wave to be focused and penetrate deep into the body and it is possible to transmit power to a deep part of the living body.

Figure 2:
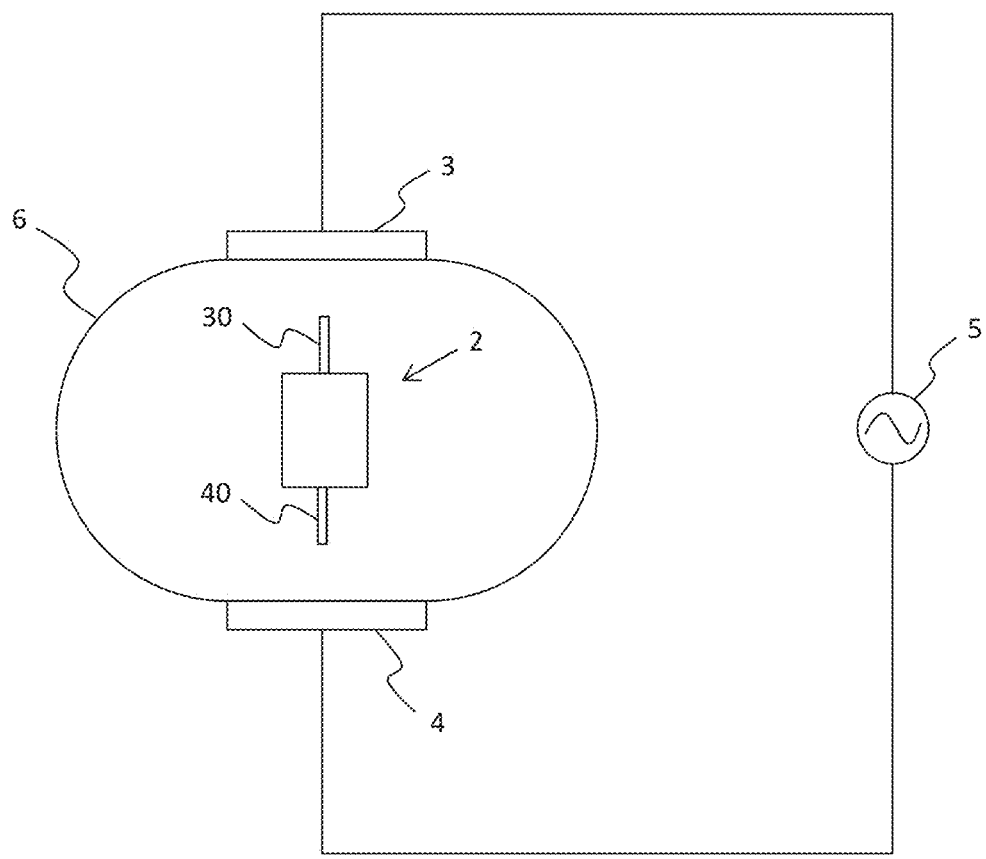
FIG. 2 is a diagram showing a system configuration of a power feed system according to a first embodiment.

FIG. 2 is a diagram showing a system configuration of a power feed system according to the present embodiment. A power feed system 1 includes: a pair of electrodes (a first surface electrode 3 and a second surface electrode 4) mounted on a surface of a living body 6; an implant electronic device 2 that is disposed in the living body 6, includes a pair of electrodes (a first body internal electrode 30 and a second body internal electrode 40), and also includes a resonant/resonance circuit, an amplifier circuit, a drive circuit and the like; and a high frequency AC power source 5 that applies a high frequency alternating voltage to the first surface electrode 3 and the second surface electrode 4. The first body internal electrode 30 and the second body internal electrode 40 of the implant electronic device 2 are brought into contact with different tissues of the living body 6 to be fixed thereto.

As shown in FIG. 2, the first surface electrode 3 and the second surface electrode 4 are stuck onto the surface of the living body 6 such that the implant electronic device 2 fixed to the deep part of the living body 6 is disposed between the respective electrodes 3 and 4. In this case, the living body 6 including the implant electronic device 2 becomes a part of the AC circuit. A potential difference is generated in the living body 6 having an impedance of 50 to 2500Ω by applying an AC voltage of 100 kHz to 4 MHz (more preferably 350 kHz to 475 kHz which is easy to penetrate into a living body) to the first surface electrode 3 and the second surface electrode 4 sandwiching the living body 6 by the high frequency AC power source 5. A current flows between the first body internal electrode 30 and the second body internal electrode 40 which are in contact with the different tissues (tissues having different electric potentials) of the living body 6 by lowering the impedance of the implant electronic device 2 to 1/10 or less (for example, 5 to 250Ω or less, more preferably 10Ω or less) of a biological resistance. The resultant current is amplified by the resonant/resonance and amplifier circuits to supply sufficient power to a drive part (such as LED, for example).

In addition, it is desirable to make resistance values of the first surface electrode 3 and the second surface electrode 4 equal to or less than a ground resistance (the resistance value of the ground earth), desirably 50Ω or less, for example.

Further, the implant electronic device 2 does not need to have the resonant/resonance circuit or the amplifier circuit. The implant electronic device 2 may have a configuration only having at least the drive part.

When the implant electronic device 2 is introduced into the living body 6, the first body internal electrode 30 and the second body internal electrode 40 are fixed while in contact with the inside of the living body 6. In this state, a high frequency voltage is applied to the living body 6 through the first surface electrode 3 and the second surface electrode 4 stuck onto the surface of the living body 6, by the high frequency AC power source 5. This generates a potential difference in the living body 6.

Figure 3A:
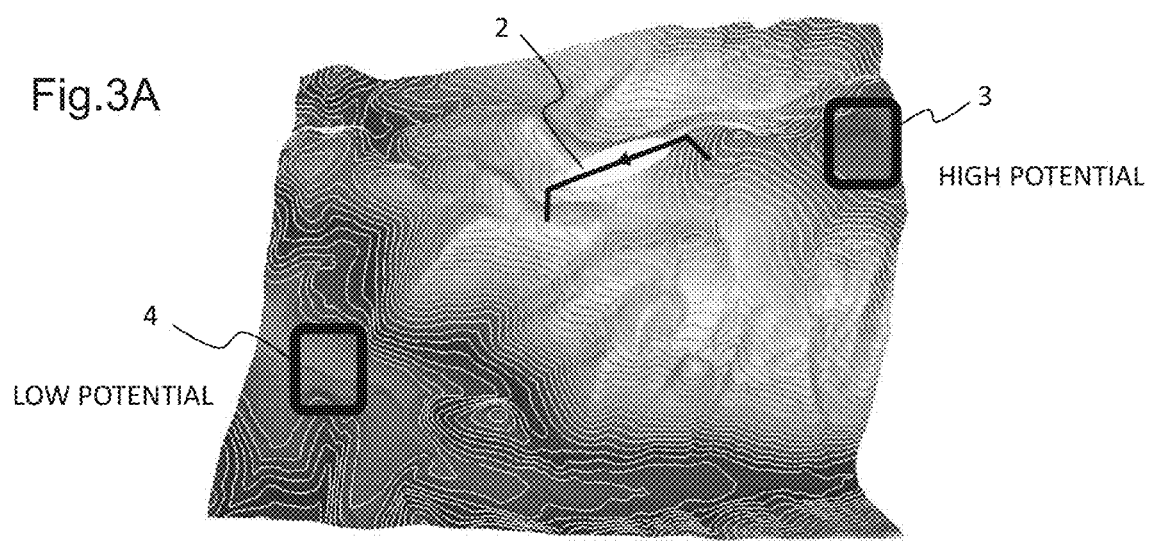
FIGS. 3A to 3C are diagrams showing a potential difference within a living body.
Figure 3B:
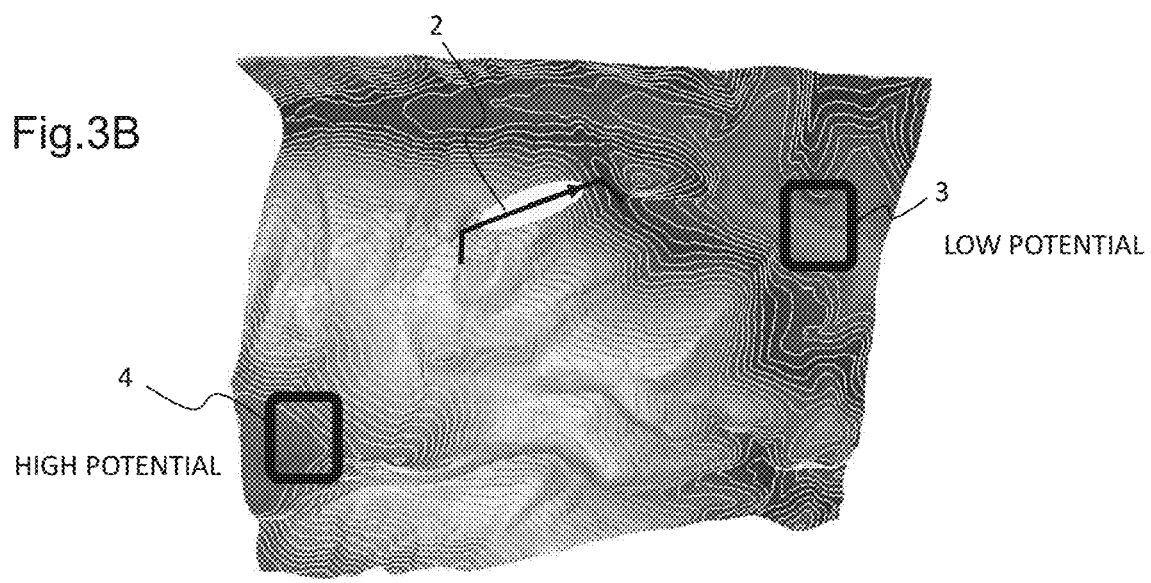
Figure 3C:
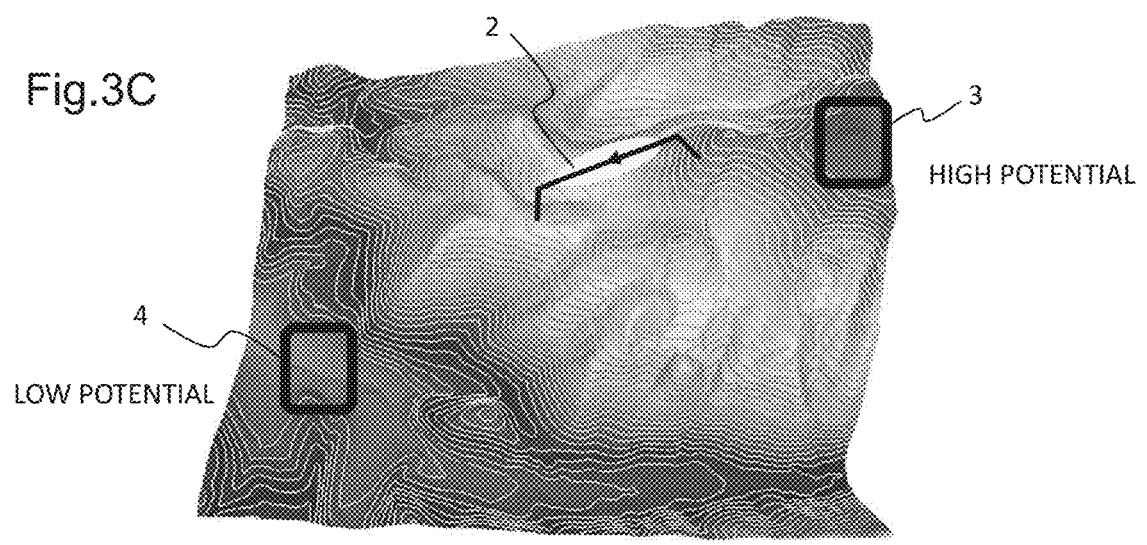

FIGS. 3A to 3B are diagrams showing an example of a potential difference in a living body when a high frequency voltage is applied. FIGS. 3A to 3C are in chronological order and represent the respective potential differences generated in the living body at certain moments using a contour. Note that in FIGS. 3A to 3C, there are densely concentrated portions on both sides for the convenience of the application form (gray scale), but actually, they change continuously "thin to dense" or "dense to thin" from one side to the other.

As shown in FIGS. 3A to 3C, by applying the high frequency alternating voltage, the potential at the first surface electrode 3 side is high and the potential at the second surface electrode 4 side is low at a certain moment, and at the next moment when polarity changes, the high potential and the low potential are interchanged. In such a state, the first body internal electrode 30 and the second body internal electrode 40 are in contact with the places having different electric potentials, and a current flows in the implant electronic device 2 due to a potential difference generated on both ends of the implant electronic device 2 and thereby power is supplied.

Hereinafter, the sandwiching method power feed system according to the present embodiment will be described in more detail. As described above, the tissue in the living body 6 and the electrodes (the first body internal electrode 30 and the second body internal electrode 40) of the implant electronic device 2 need to be in contact with each other at two different points, and a current corresponding to a contourlike potential difference generated in the living body tissue having rated load of 350Ω (50 to 2500Ω) is drawn into the implant electronic device 2 to supply power to the same. Since the contour of the potential difference in the living body tissue instantaneously interchanges, the possibility that points with which the first body internal electrode 30 and the second body internal electrode 40 are in contact are on the same contour line in the living body 6 is extremely low, and a potential difference is always generated between the two points. In this case, in order to obtain a larger potential difference, it is desirable that the distance between the two points where the first body internal electrode 30 and the second body internal electrode 40 are in contact with the living body tissue is as long as possible.

A circuit part other than the contact points where the first body internal electrode 30 and the second body internal electrode 40 are in contact with the living body tissue is insulated from the living body tissue. This insulated part is configured so as not to cause insulation breakdown even with electric power of about 120 W (current 1A, voltage 2000 V), for example.

In addition, as a specific example of the implant electronic device 2, it may be an advanced drive device, such as an IC chip or MEMS (Micro Electro Mechanical Systems), designed for a light emitting diode, a heat generating diode, a nerve stimulating device, a biometric information sensor such as a pH sensor, an artificial sensing device such as a cochlear implant, an artificial retina, or an artificial spinal cord, or a device to be an artificial organ such as an artificial anal sphincter, an artificial heart, a self-moving endoscope, or a micro robotic surgery, for example. Further, a memory that records information obtained by these devices may be provided. Furthermore, these devices may be provided with a function of storing electric power by a secondary battery or the like.

As described above, in the power feed system according to the present embodiment, the high frequency alternating voltage applied between the pair of electrodes makes it possible to cause a current to flow using the potential difference of the living body, and then it is possible to stably and sufficiently supply electric power to the electronic device attached deep within the living body to drive it by an external power supply. Further, since it does not require a battery, it is possible to make the electronic device small in size.

Other Embodiment

A power feed system according to the present embodiment will be described with reference to FIGS. 4 to 9B. This embodiment shows some variations of the implant electronic device 2 in the first embodiment. In the present embodiment, description overlapping with the first embodiment will be omitted.

Figure 4:
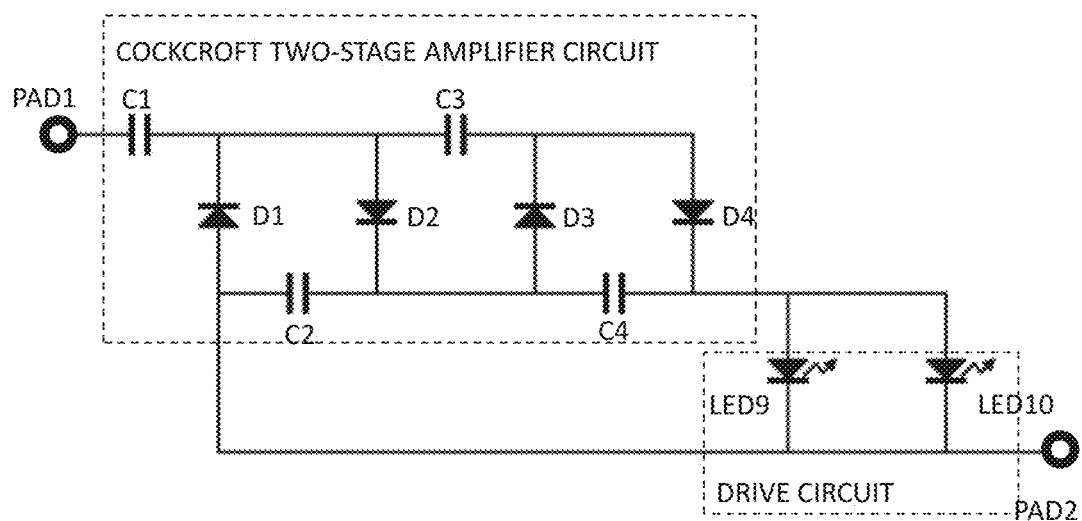
FIG. 4 is a first diagram showing an example of a circuit configuration of an implant electronic device.

FIG. 4 is a first diagram showing an example of a circuit configuration of an implant electronic device. The implant electronic device 2 has a basic circuit composed of a booster rectifier circuit (Cockcroft two-stage amplifier circuit) and a drive circuit (light emitting diode (LED) in the case of FIG. 4). This is a configuration such that more current flows by having the Cockcroft amplifier circuit. In this case, if the number of stages of the Cockcroft amplifier circuit is increased, it is possible to increase the amount of current to be supplied by increasing the amplification factor, but in some cases it may occur that the impedance of the circuit itself increases and the amplification efficiency is not good.

That is, an appropriate value exists in the number of stages of the Cockcroft amplifier circuit according to the magnitude of parasitic components (for example, components including a parasitic capacitance, a parasitic resistance and the like) of a coil, a capacitor, and a diode of the amplifier circuit, and it is possible to more efficiently supply a current by determining the appropriate number of stages according to the parasitic components to configure the circuit.

Further, in this case, it may be provided with a resonance circuit having at least one stage or more, which is composed of a coil and a capacitor and whose resonance frequency satisfies $f=1/(2\pi\sqrt{(LC)})$, where f is a frequency of the high frequency alternating voltage applied to the high frequency AC power source 5, L is a self-inductance of the coil, and C is a capacitance of the capacitor.

Figure 5:
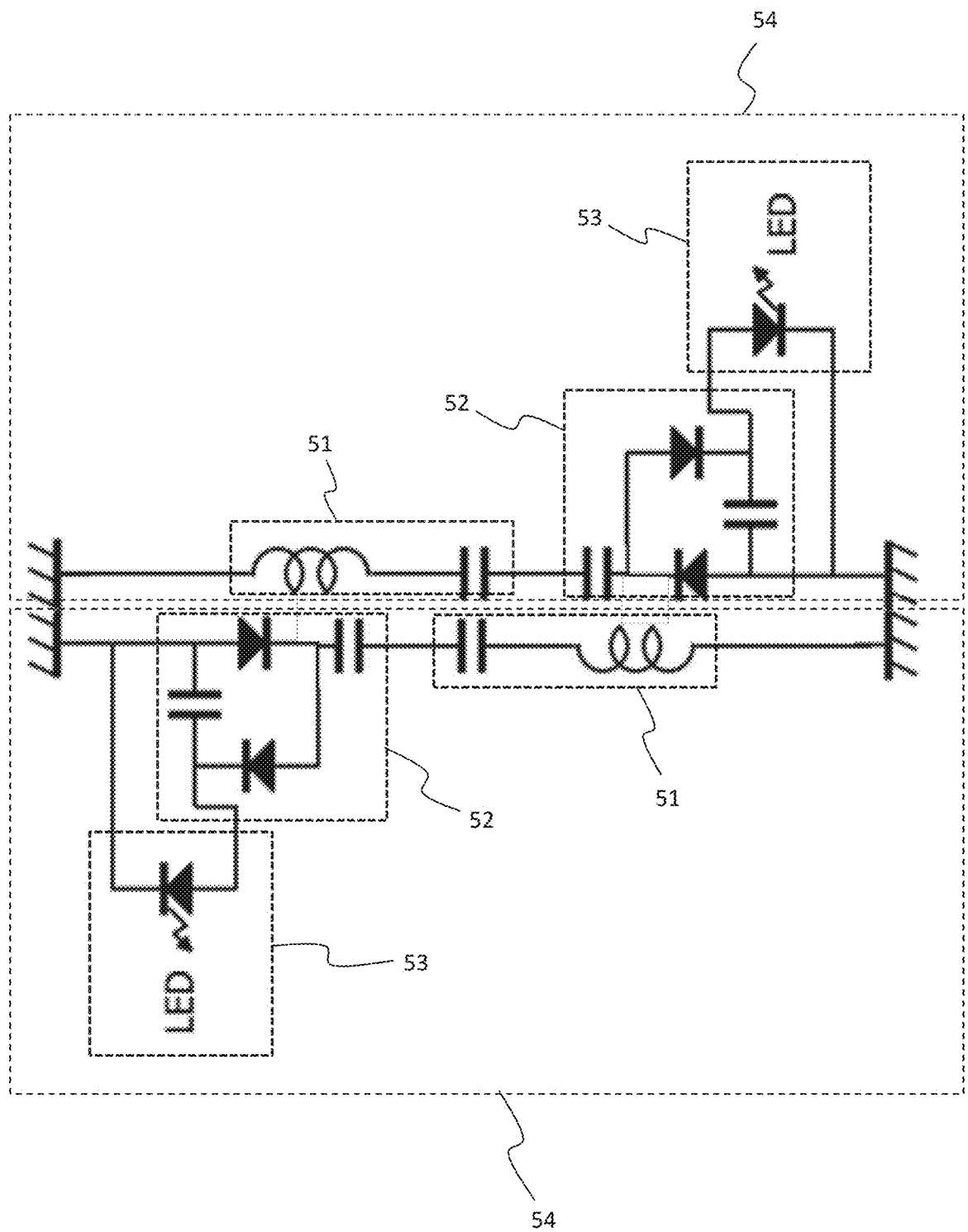
FIG. 5 is a second diagram showing an example of a circuit configuration of an implant electronic device.

FIG. 5 is a second diagram showing an example of a circuit configuration of an implant electronic device. In the implant electronic device 2, basic circuits 54 each composed of an LC resonance circuit 51, a Cockcroft single-stage amplifier circuit 52, and a drive circuit 53 (light emitting diode (LED) in the case of FIG. 5) are juxtaposed so as to be mutually opposite in polarity, so that one of the basic circuits 54 emits light at the positive polarity of the high frequency AC power source 5 and the other emits light at the negative polarity.

Note that in FIG. 5, two basic circuits 54 are juxtaposed so as to have opposite polarities, but it may be configured with only one basic circuit 54. Further, in FIG. 5, the light emitting diode is illustrated by an example as the drive circuit 53, but as described in the first embodiment, an advanced drive device such as an IC chip or MEMS (Micro Electro Mechanical Systems) may be used depending on the other intended use (for example, a heat generating diode, a nerve stimulating device, a biometric information sensor such as a pH sensor, an artificial sensing device such as a cochlear implant, an artificial retina, or an artificial spinal cord, or a device to be an artificial organ such as an artificial anal sphincter, an artificial heart, a self-moving endoscope, or a micro robotic surgery). Further, a memory that records information obtained by these devices may be provided. Furthermore, these devices may be provided with a function of storing electric power by a secondary battery or the like.

Further, in a case where the two basic circuits 54 are juxtaposed so as to have opposite polarities and the light emitting diodes are used as the drive circuits 53 as shown in FIG. 5, it may be configured such that one of the light emitting diodes is arranged on the front surface side of a substrate and the other light emitting diode is arranged on the rear surface side of the substrate. By doing so, it is possible to prevent light emission of the light emitting diodes from being interrupted by a shadow of the substrate.

Figure 6:
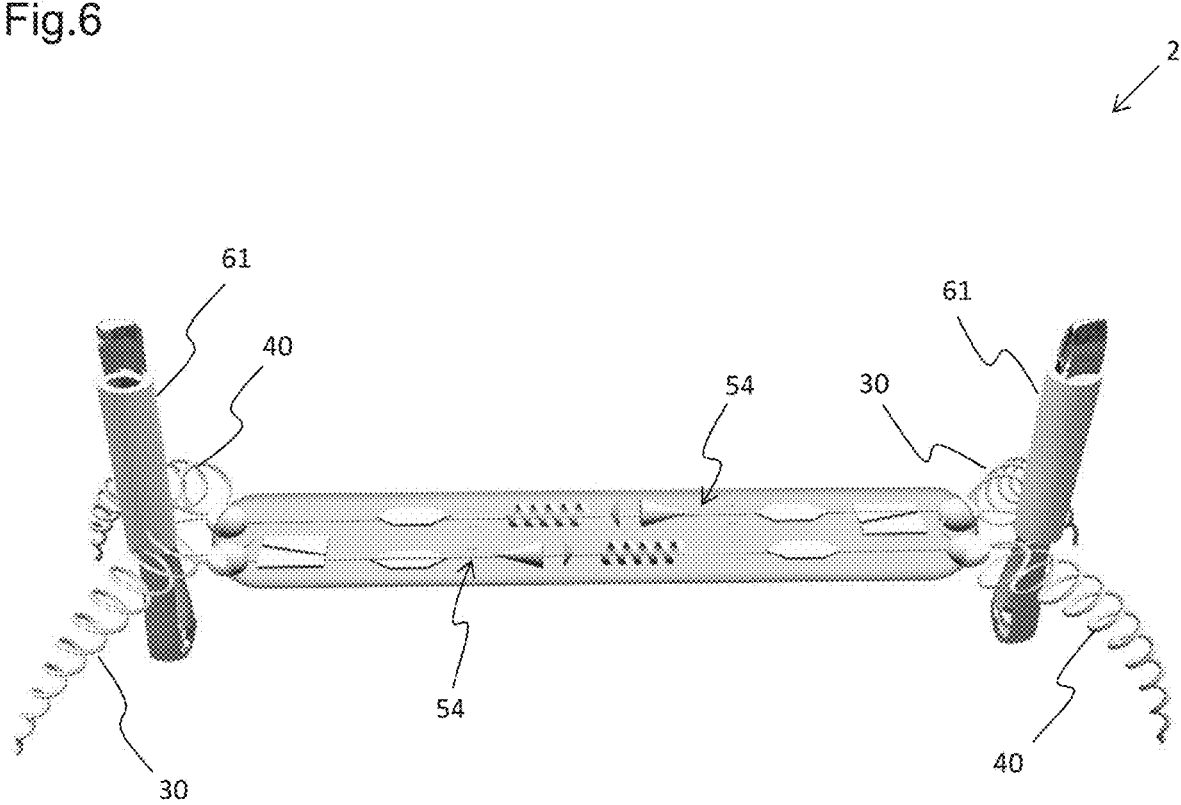
FIG. 6 is a first schematic diagram showing an example of a structure of an implant electronic device.

FIG. 6 is a first schematic diagram showing an example of a structure of an implant electronic device. The basic circuits 54 shown in FIG. 5 are juxtaposed so as to have mutually opposite polarities, and the first body internal electrode 30 and the second body internal electrode 40 are arranged in a spiral shape at both ends of the respective basic circuits 54. Clips 61 for fixing to the living body tissue are arranged at both ends of each basic circuit 54. These clips 61 can also function as electrodes by being electrically connected to the respective basic circuits 54.

Figure 7A:
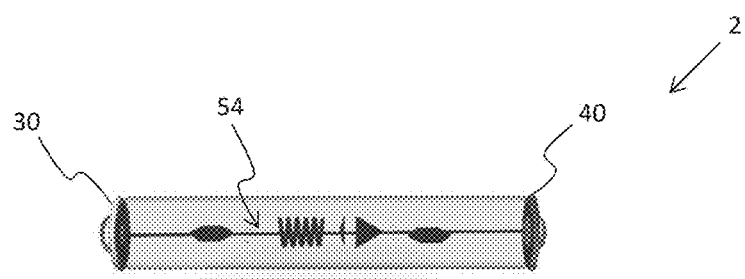
FIGS. 7A and 7B are diagrams showing spiral electrodes constituting an implant electronic device.
Figure 7B:
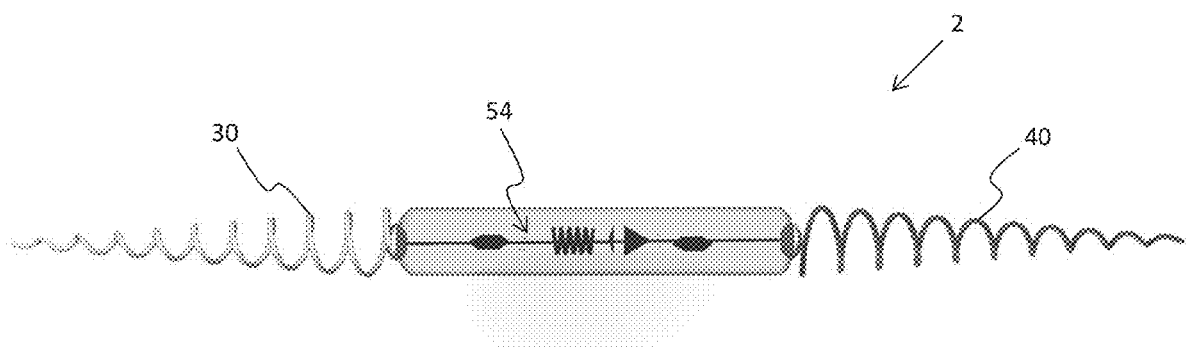

FIGS. 7A and 7B are diagrams showing spiral electrodes constituting an implant electronic device. FIGS. 7A and 7B show a case where the basic circuit 54 is constituted by a single-wire circuit. The spiral electrodes are compressed in a closed state before inserted into the living body 6 (FIG.

7A) and, after inserted into the living body 6, the spiral electrodes extend to an open state due to the influence such as its body temperature and/or pressure (FIG. 7B). That is, the spiral electrodes can move smoothly in a forceps hole of a flexible endoscope before inserted into the living body 6 by making the spiral electrodes to be in such a shape as shown in FIG. 7A, and are released at the time of entry into the living body 6 through the forceps hole, so that it is possible to bring the respective spiral electrodes into contact with parts having different electric potentials in the living body 6 such that the potential difference between them is as large as possible. In addition, it is desirable to use a shape-memory alloy or the like as a material of the spiral electrodes to realize such a behavior.

Figure 8A:
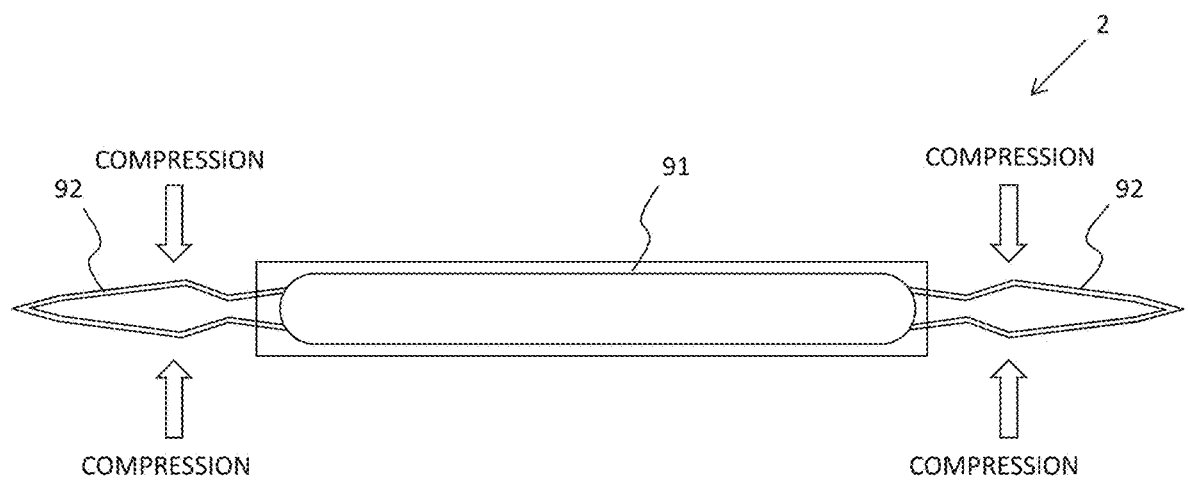
FIGS. 8A and 8B are second schematic diagrams showing an example of a structure of an implant electronic device.
Figure 8B:
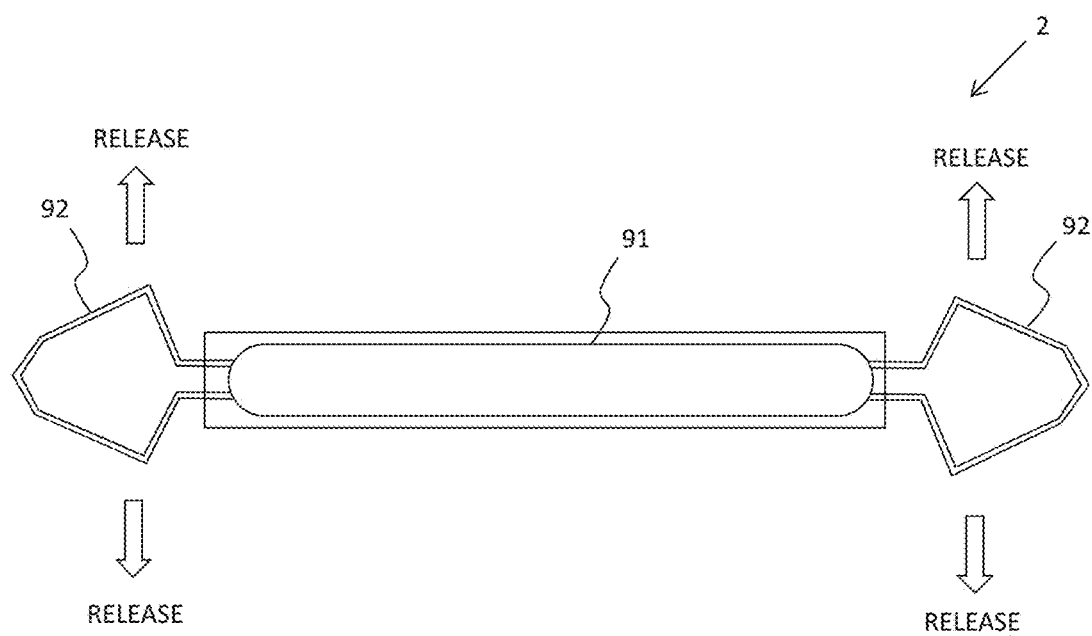

FIGS. 8A and 8B are second schematic diagrams showing an example of a structure of an implant electronic device. FIG. 8A shows a structure in a case where engaging parts before inserted into the living body 6 are compressively deformed, and FIG. 8B shows a structure in a case where the engaging parts are expanded in the living body 6. In FIGS. 8A and 8B, an implant electronic device 2 includes: circuitry 91 composed of the basic circuit 54; and engaging parts 92 that are electrically connected to the basic circuit 54 at both longitudinal ends of the circuitry 91 and that engage with clips 61 as a holding member for fixing the implant electronic device 2 in the living body 6.

Figure 9A:
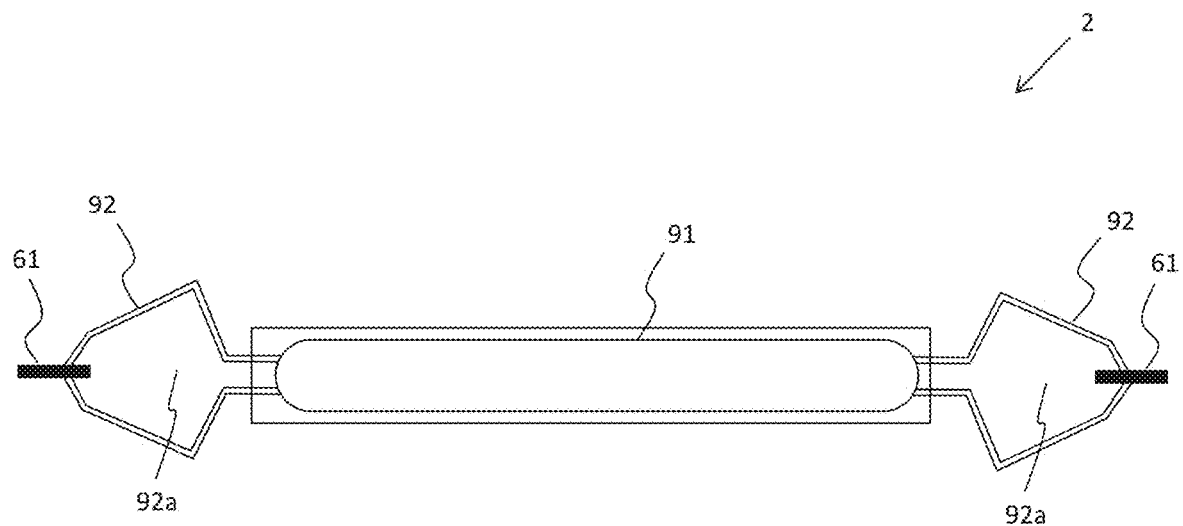
FIGS. 9A and 9B are diagrams showing a state in which an implant electronic device is fixed in a living body.

The engaging parts 92 have a flexible structure by twisting a plurality of wires into a single wire. As shown in FIG. 9A, the engaging parts 92 are compressively deformed to allow the implant electronic device 2 to smoothly pass through the endoscopic forceps hole prior to insertion into the living body 6. Specifically, the engaging parts 92 are compressively deformed into an elongated shape such that the same direction as a longitudinal direction of the implant electronic device 2 coincides with a longitudinal direction of the engaging part 92. In this state, the implant electronic device 2 is introduced into the living body 6 through the endoscopic forceps hole.

Figure 9B:
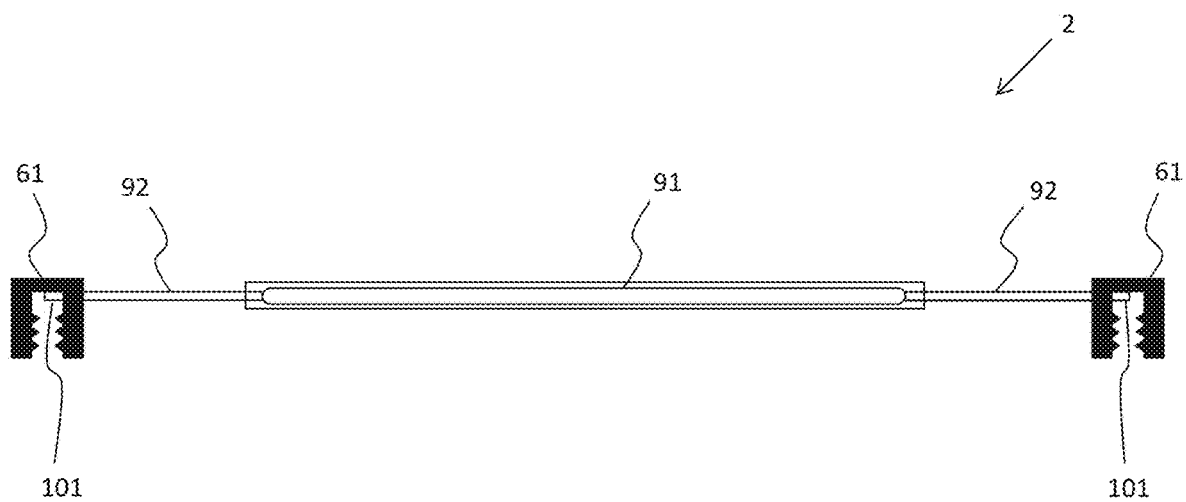

After the implant electronic device 2 is discharged from the endoscopic forceps hole in the living body 6, the implant electronic device 2 expands to a structure as shown in FIG. 8B due to the flexibility of the engaging parts 92. FIGS. 9A and 9B are diagrams showing a state in which an implant electronic device is fixed in a living body. FIG. 9A is a top view and FIG. 9B is a side view. The implant electronic device is fixed in the living body in such state that one end of the respective clip 61 is passed through an engaging region 92a of the respective engaging part 92 and a tip 101 of the respective engaging part 92 is in contact with the respective clip 61, while being in a state where the engaging parts 92 are expanded, as shown in FIGS. 9A and 9B. The tips 101 of the engaging parts 92 in contact with the clips 61 are not insulated and are in a state of being electrically connected to the clips 61. The clips 61 have conductivity and are inserted into the living body tissue to fix the implant electronic device 2 in the living body 6 and to electrically connect the living body tissue and the implant electronic device 2.

As described above, in the power feed system according to the present embodiment, the first body internal electrode 30 and the second body internal electrode 40 of the implant electronic device 2 are arranged at both longitudinal ends of the implant electronic device 2, and it is provided with the engaging parts 92 that engage with the conductive clips 61 inserted into the tissue of the living body 6, so that it is possible to firmly fix the implant electronic device 2 to necessary parts in the living body 6.

Further, since the first body internal electrode 30 and the second body internal electrode 40 are arranged at both longitudinal ends of the implant electronic device 2, it is possible to fix the implant electronic device 2 in the living body 6 such that the potential difference between the first body internal electrode 30 and the second body internal electrode 40 is as large as possible.

Further, since the respective engaging parts 92 are made of a flexible conductive metal body that is deformable by compression into an elongate shape such that the same direction as the longitudinal direction of the implant electronic device 2 coincides with the longitudinal direction of the respective engaging parts 92, it is possible to carry the electronic device 2 including electrodes at both ends thereof into the body through a forceps hole of an endoscope used for endoscopic surgery or the like and to, after carrying it to a predetermined part, expand the engaging parts 92 to hold the implant electronic device 2 by the clips 61, resulting in that it is possible to attach the implant electronic device 2 within the body while minimizing the burden on a patient.

In addition, it is desirable that the entire circuit including the contact part and the insulated part of the first body internal electrode 30 and the second body internal electrode 40 is in a cylindrical shape with a major diameter of 2.2 mm or less in order to facilitate the insertion of the implant electronic component 2 into the living body 6. Further, it is desirable that the height of the cylindrical circuit at the time of being inserted into the living body 6 is about 10 mm or less. Furthermore, it is desirable that the surface is smooth and not viscous.

Further, existing clips 61 that are generally available in the market may be used for the contact with living body tissues. The existing clips 61 include those made entirely of steel use stainless (SUS), those in which resin is used in connections, and those in which tip contact parts are made of metal, for example, either one of which may be used. In this case, it is desirable that the implant electronic device 2 can be inserted with a delivery appliance similar to the clip 61.

EXAMPLES

The following experiments were conducted on the power feed system according to the present invention.

(1) LED Light Emission

Experiments were carried out as to whether the LED(s) of the implant electronic device 2 embedded in the living body by the sandwiching method, a grounding method, and a one-side method, respectively. Devices for an electric scalpel were diverted to the high frequency AC power source 5 and the electrodes (the first surface electrode 3 and the second surface electrode 4). The configuration of experimental equipment was as follows.

(1) Round chicken as the living body 6
(2) Electrodes for an electric scalpel as the first surface electrode 3 and the second surface electrode 4
(3) High frequency generator for the electric scalpel as the high frequency AC power source 5
(4) The implant electronic device 2 (the basic circuit 54 composed of the resonant/resonance and amplifier circuits and the LED; and two electrodes of the first body internal electrode 30 and the second body internal electrode 40)
(5) Optical sensor (power meter)

Figure 10:
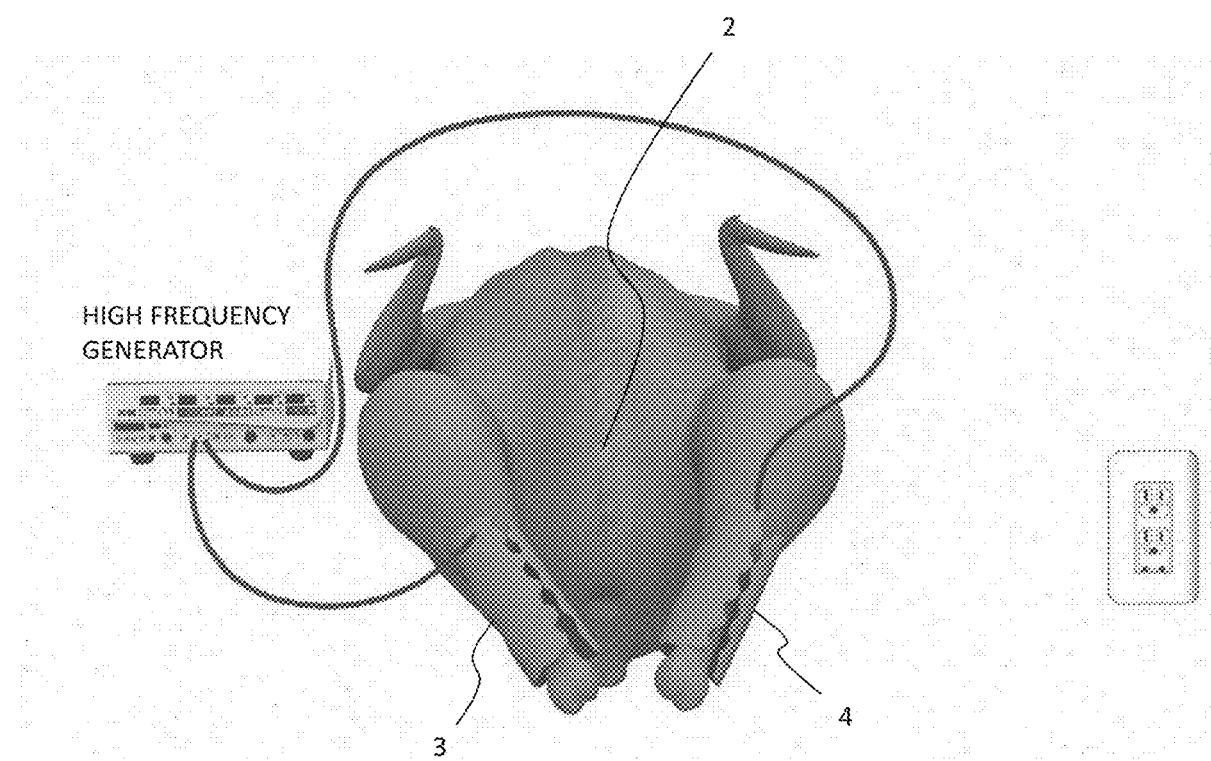
FIG. 10 is a view showing a state of an experiment of a sandwiching method (ungrounded)

Hereinafter, an experimental method of the sandwiching method (ungrounded) will be described. FIG. 10 is a view showing a state of an experiment of the sandwiching method (ungrounded). At first, the first surface electrode 3 was attached to one leg of one round chicken and the second surface electrode 4 was attached to the other leg. The implant electronic device 2 was placed in the abdominal cavity of the round chicken, and the two of the first body internal electrode 30 and the second body internal electrode 40 were brought into contact with the living body tissue. The power source of the High frequency generator was turned on. When the LED turned on, it was measured with the power meter. With respect to the amplifier circuit, the light intensity of the LED was measured using three types of implant electronic devices 2: one with a Cockcroft single-stage circuit; one with a Cockcroft two-stage circuit; and one without any amplifier circuits.

Figure 11:
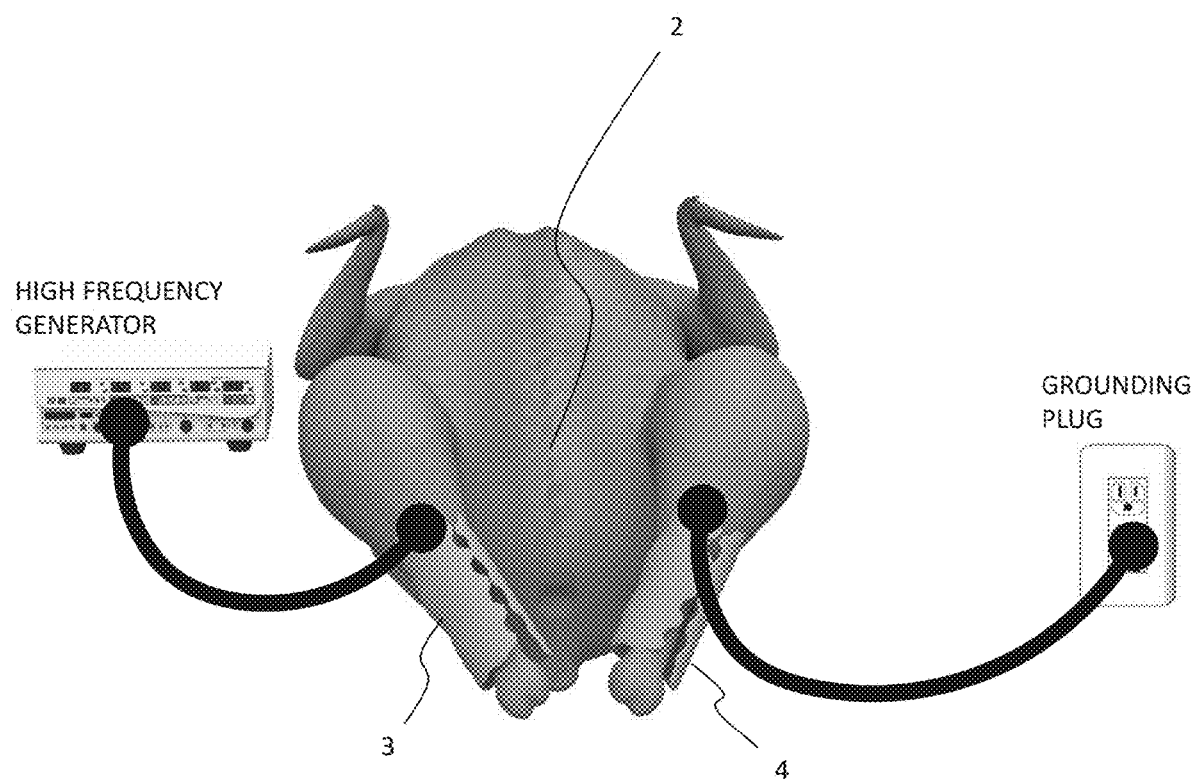
FIG. 11 is a view showing a state of an experiment of a sandwiching method (grounded)

Next, an experimental method of the sandwiching method (grounded) will be described. FIG. 11 is a view showing a state of an experiment of the sandwiching method (grounded). At first, the first surface electrode 3 was attached to one leg of the round chicken and the second surface electrode 4 was attached to the other leg. The implant electronic device 2 was placed in the abdominal cavity of the round chicken, and the two of the first body internal electrode 30 and the second body internal electrode 40 were brought into contact with the living body tissue. The second surface electrode 40 of the round chicken was grounded (connected to a grounding plug). The power source of the High frequency generator was turn on. When the LED turned on, it was measured with the power meter. With respect to the amplifier circuit, the light intensity of the LED was measured using three types of implant electronic devices 2; one with a Cockcroft single-stage circuit; one with a Cockcroft two-stage circuit; and one without any amplifier circuits.

Figure 12:
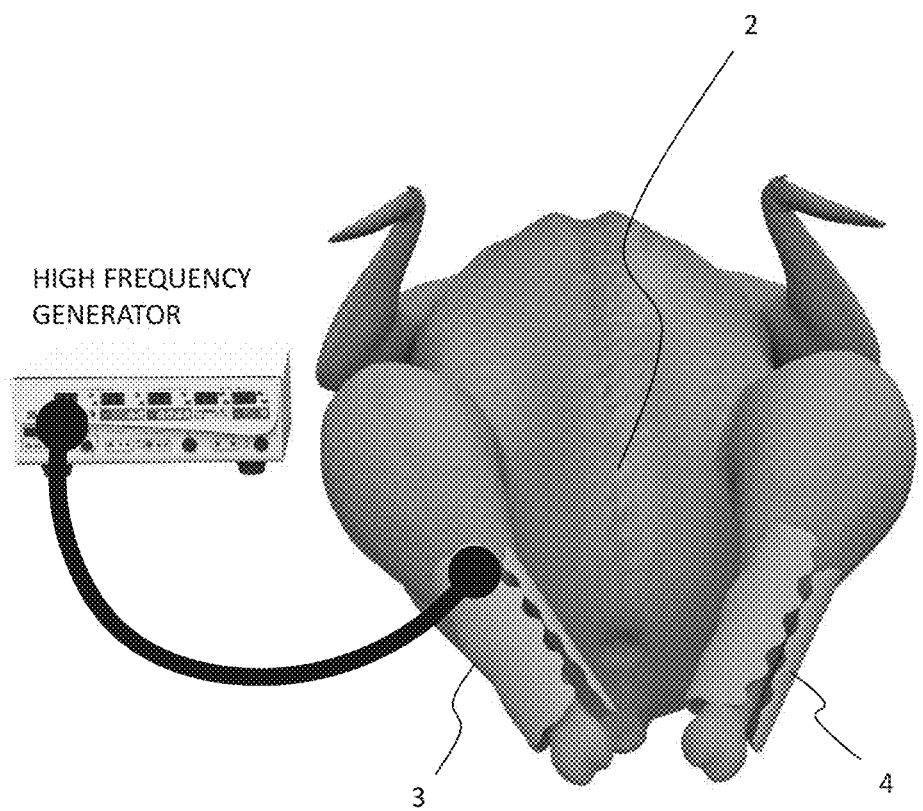
FIG. 12 is a view showing a state of an experiment of a one-side method (grounded)

Next, an experiment method of the one-side method will be described. FIG. 12 is a view showing a state of an experiment of the one-side method (grounded). At first, the first surface electrode 3 was attached to one leg of the round chicken. The implant electronic device 2 was placed in the abdominal cavity of the round chicken, and the two of the first body internal electrode 30 and the second body internal electrode 40 were brought into contact with the living body tissue. The power source of the High frequency generator was turned on. When the LED turned on, it was measured with the power meter. With respect to the amplifier circuit, the light intensity of the LED was measured using three types of implant electronic devices 2: one with a Cockcroft single-stage circuit; one with a Cockcroft two-stage circuit; and one without any amplifier circuits.

Figure 13:
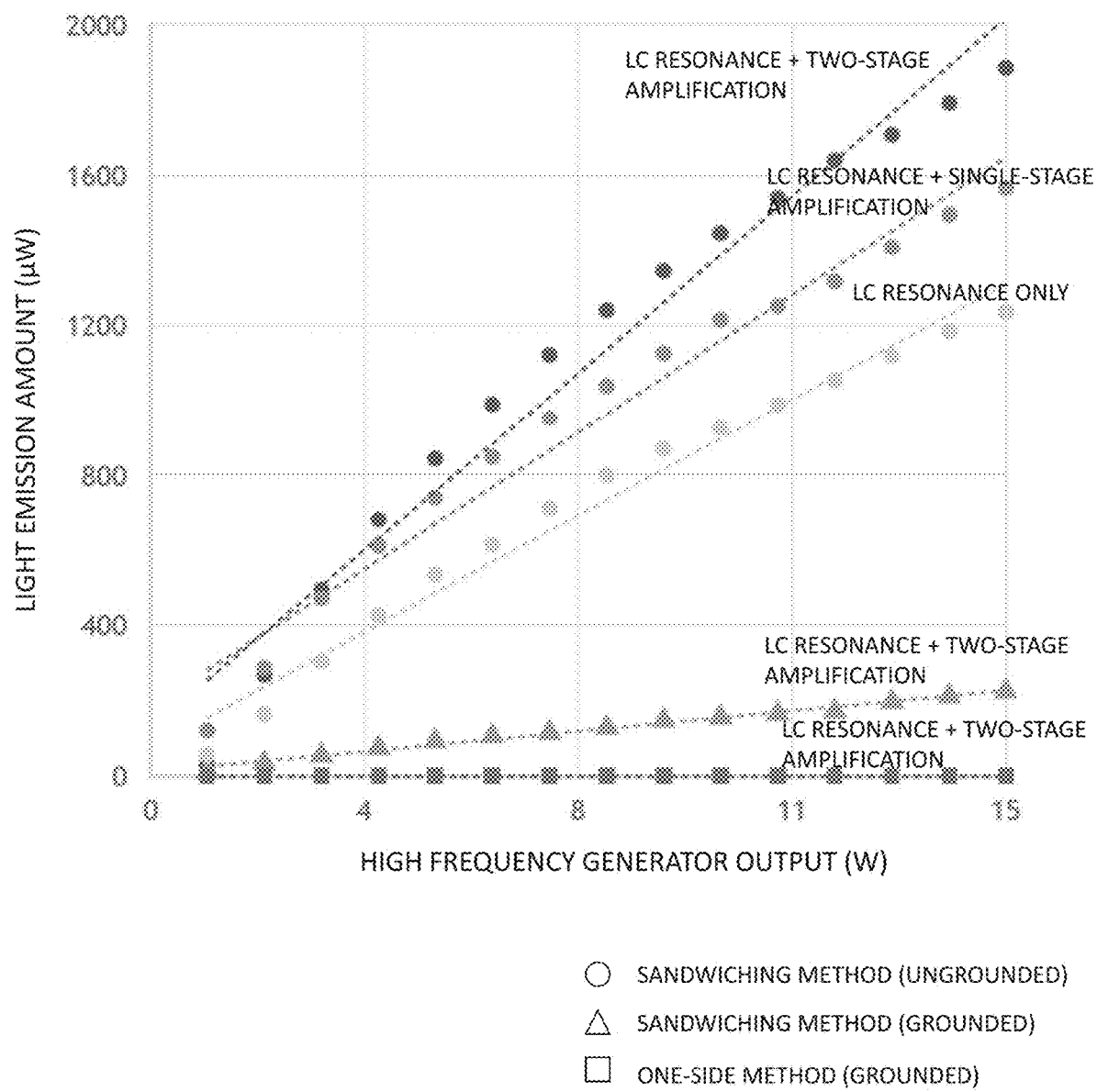
FIG. 13 is a diagram showing experimental results of FIGS. 10 to 12.

FIG. 13 is a diagram showing results of the above experiments. The horizontal axis represents an output of the High frequency generator, and the vertical axis represents a light emission amount of the LED fitted in the implant electronic device 2 measured with the optical sensor (power meter). In the sandwiching method (ungrounded), it has been revealed that the light emission amount of the LED increases in proportion to the output of the High frequency generator. The light emission amount of the LED was larger in a case where the number of stages of the Cockcroft circuit, which is the amplifier circuit, is two rather than one. This is because the amplification factor is higher. Note that when the number of stages of the Cockcroft circuit is further increased, the impedance of the circuit itself increases and the amplification efficiency decreases.

In the sandwiching method (grounded), even if the output of the High frequency generator was increased, the light emission amount of the LED only increased slightly, and a current could not be supplied effectively. In the one-side method, the amount of light emission was not measured. Note that in FIG. 13, only data in the case of Cockcroft two-stage circuit having the largest amount of light emission is described for the sandwiching method (grounded) and the one-side method.

Figure 14:
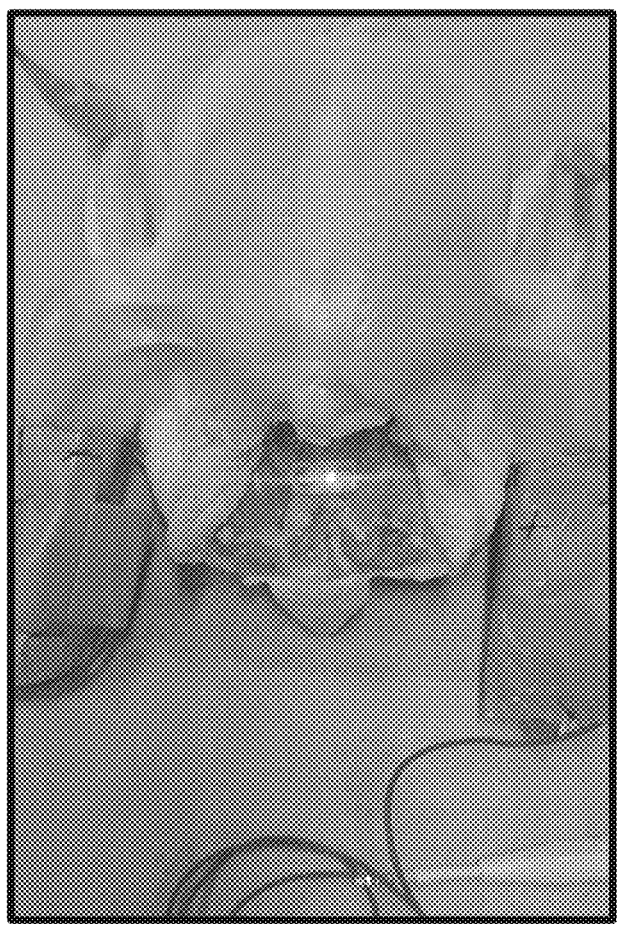
FIG. 14 shows images of an actual experiment system.
Figure 14:
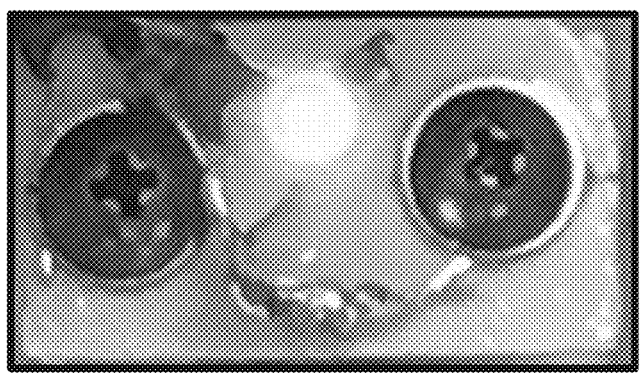
Figure 15A:
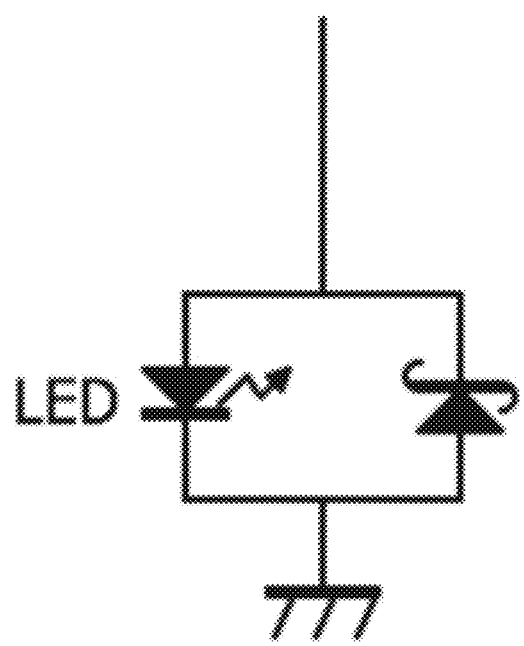
FIGS. 15A and 15B are first diagrams showing combination examples of an LED, a resonance circuit, and an amplifier circuit.
Figure 15B:
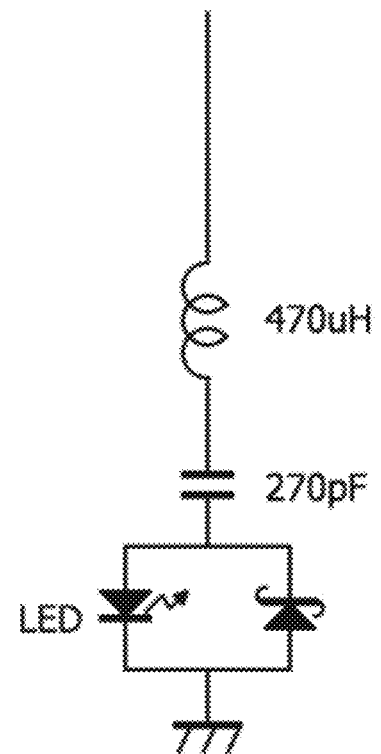
Figure 16A:
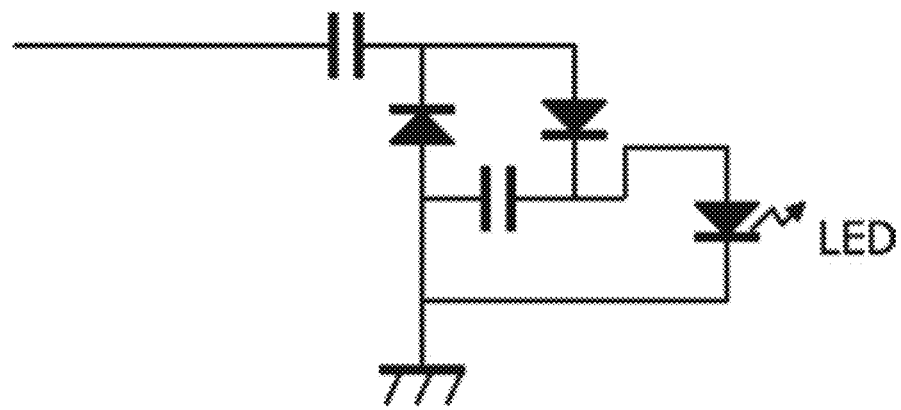
FIGS. 16A and 16B are second diagrams showing combination examples of an LED, a resonance circuit, and an amplifier circuit.
Figure 16B:
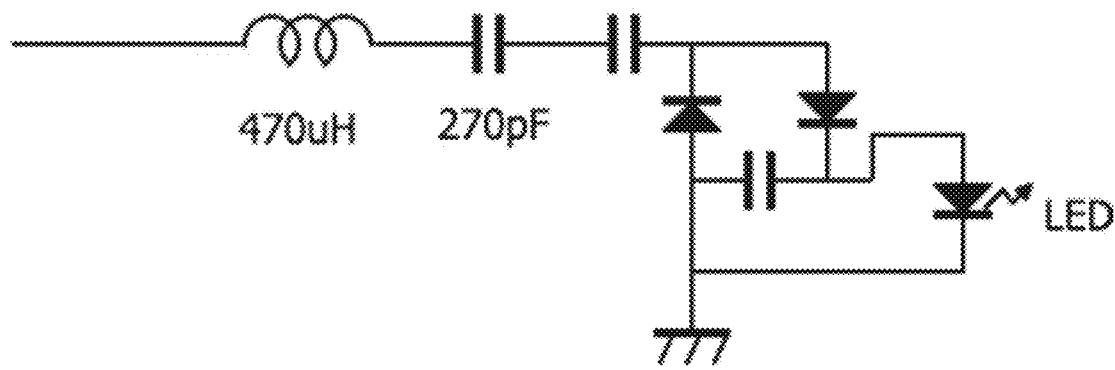
Figure 17A:
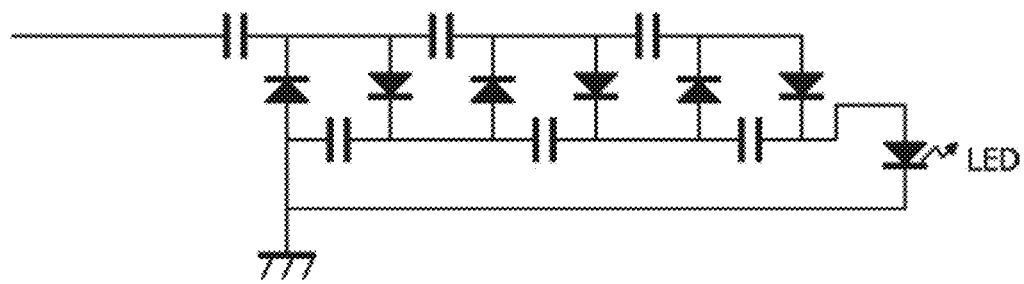
FIGS. 17A and 17B are third diagrams showing combination examples of an LED, a resonance circuit, and an amplifier circuit.
Figure 17B:
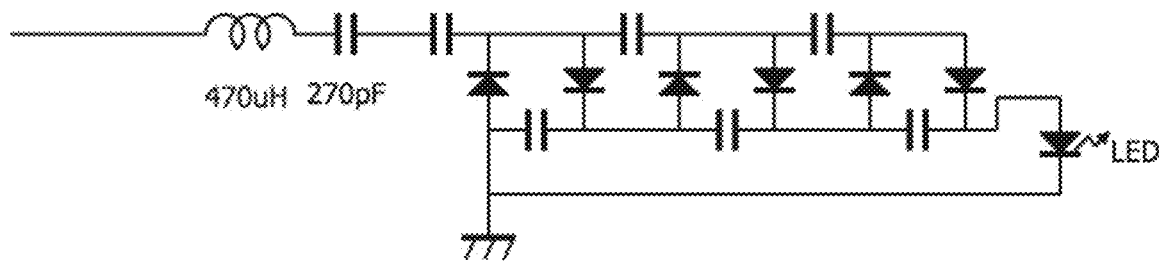

FIG. 14 shows images of an actual experiment system. It shows a state where the LED was emitting light by connecting the first surface electrode 3 and the second surface electrode 4 to the round chicken and driving the High frequency generator to supply a current to the circuit of the implant electronic device 2.

(2) Resonant Circuit, Amplifier Circuit

The LED and the resonance and amplification circuits for use in the implant electronic device 2 were combined in a plurality of patterns to measure the light emission amount of the LED. FIGS. 15A to 17B are diagrams showing combination examples of a circuit configuration. Here, with respect to (1) LED only (FIG. 15A)
(2) LED+series resonance circuit (FIG. 15B)
(3) LED+amplifier circuit (Cockcroft with a single stage) (FIG. 16A)
(4) LED+amplifier circuit (Cockcroft with a single stage)+ series resonance circuit (FIG. 16B)
(5) LED+amplifier circuit (Cockcroft with three stages) (FIG. 17A)
(6) LED+amplifier circuit (Cockcroft with three stages)+ serial resonance circuit (FIG. 17B), the light emission amount of the LED with respect to the output of the High frequency generator was measured by the sandwiching method (ungrounded), the sandwiching method (grounded), and the one-side method, respectively.

Figure 18:
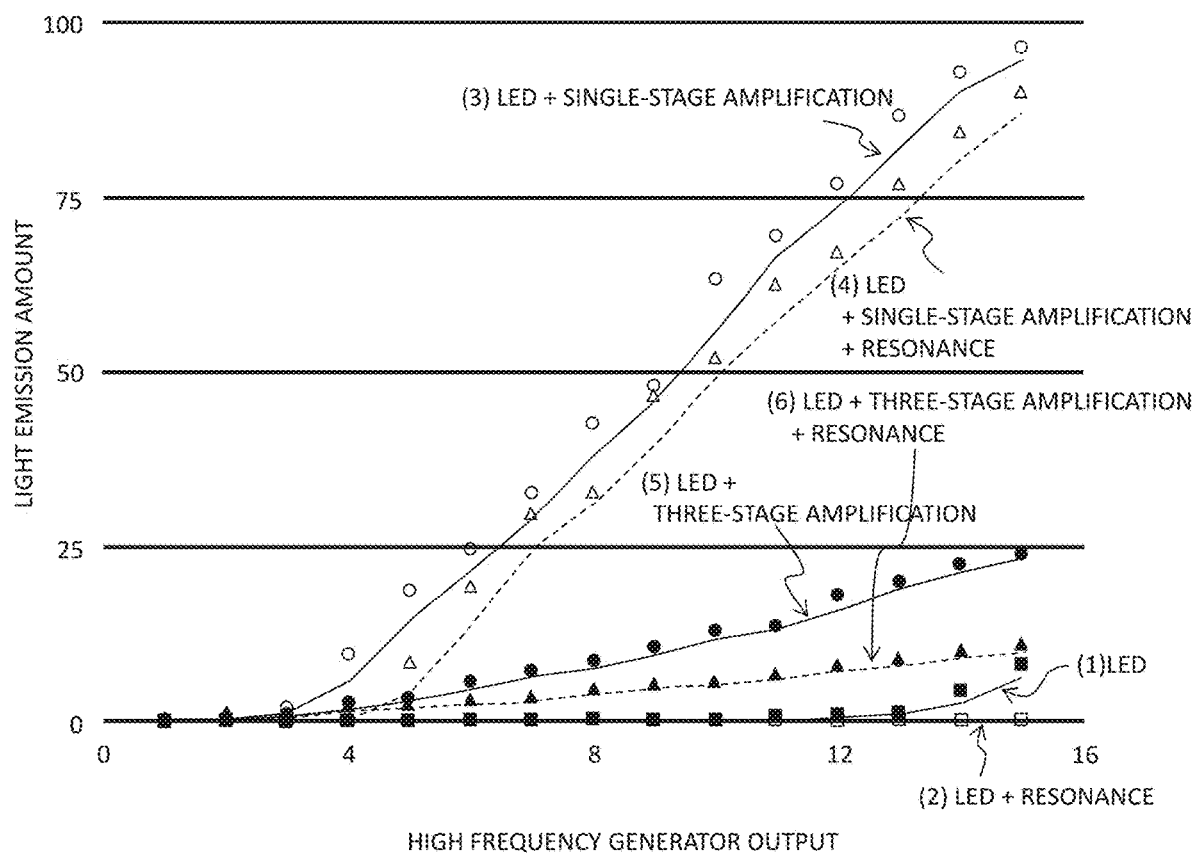
FIG. 18 is a diagram showing experimental results in the case of the sandwiching method (ungrounded)
Figure 19:
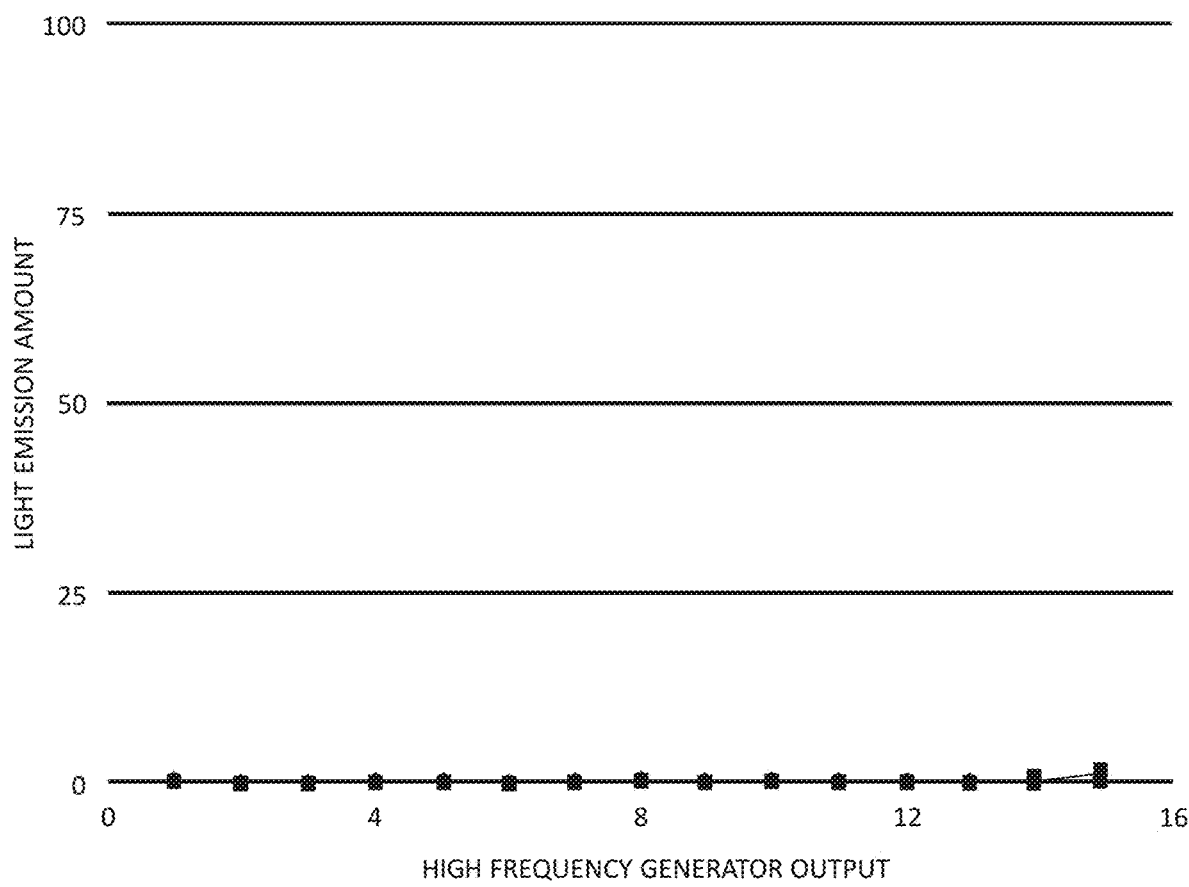
FIG. 19 is a diagram showing experimental results in the case of the sandwiching method (grounded)

FIG. 18 is a diagram showing experimental results in the case of the sandwiching method (ungrounded), FIG. 19 is a diagram showing experimental results in the case of the sandwiching method (grounded), and FIG. 20 is a diagram showing experimental results in the case of the one-side method. In each case, the amount of light emitted from the LED incorporated in the implant electronic device 2 with respect to the output of the High frequency generator was measured. The vertical axis of the graph represents the light emission amount of the LED, and the horizontal axis represents the output of the High frequency generator.

It can be seen from FIG. 19 and FIG. 20 that in the case of the sandwiching method (grounded) and the case of the one-side method, the light emission amount of the LED was small regardless of which circuit was used, and it was far from good results across the board. In contrast, as shown in FIG. 18, the Cockcroft single-stage circuit as the amplifier circuit had the largest amount of light emission in the case of the sandwiching method (ungrounded). The Cockcroft with three stages can more amplify a voltage, but an electrical resistance increases with an increase in the number of stages of amplification, so that the amount of current was smaller than that in the case of the Cockcroft with the single stage and the light emission amount of the LED was smaller.

From the above, it is apparent that it is possible to supply a current best by using the Cockcroft with the single stage or two stages as the amplifier circuit in the sandwiching method (ungrounded).

In addition, it has been revealed that the amount of light emission is larger in a case where the resonance circuit is not provided than in a case where the resonance circuit is provided, as shown in FIG. 18. This is considered because a voltage is increased by the resonance circuit, but an electrical resistance is more increased, as described above. However, it is considered that it is possible to increase electric power to be supplied to the implant electronic device by having the resonance circuit, by performing strict and highly accurate control so as to substantially match the resonance frequency.

REFERENCE SIGNS LIST

1 Power feed system
2 Implant electronic device
3 First surface electrode
4 Second surface electrode
5 High frequency AC power source
6 Living body
30 First body internal electrode
40 Second body internal electrode
51 Resonance circuit
52 Amplifier circuit
53 Drive circuit
54 Basic circuit
61 Clip
91 Circuitry
92 Engaging part
92a Engaging region
101 Tip

The invention claimed is:

1. A power feed system comprising:
an implant electronic device that is configured to be disposed within a living body;
a pair of surface electrodes that, when the implant electronic device is within the living body, are configured to come into contact with a surface of the living body; and
a power source that, when the implant electronic device is within the living body, is configured to apply a high frequency alternating voltage between the surface electrodes to supply electric power from outside of the living body to the implant electronic device within the living body while remaining outside the living body,
wherein the implant electronic device comprises a first electrode and a second electrode, the first electrode and the second electrode being fixed to respective positions having different electric potentials in the living body, and
wherein the power source applies a high frequency signal of 100 kHz to 4 MHz.

2. The power feed system according to claim 1, wherein the first electrode and the second electrode of the implant electronic device are arranged at both longitudinal ends of the implant electronic device.

3. The power feed system according to claim 1, wherein a part of the implant electronic device other than where the first electrode and the second electrode are fixed in the living body is insulated.

4. The power feed system according to claim 1, wherein a resistance value of the pair of surface electrodes is equal to or less than a ground resistance.

5. The power feed system according to claim 1, wherein a resistance value of the implant electronic device is 1/10 or less of a biological resistance.

6. The power feed system according to claim 1, wherein the implant electronic device includes an amplifier circuit having at least one stage or more.

7. The power feed system according to claim 1, wherein the implant electronic device comprises a light emitting diode, a heat generating diode, a nerve stimulating device, a biometric information sensor, a cochlear implant, an artificial retina, an artificial spinal cord, an artificial anal sphincter, an artificial heart, a self-moving endoscope, and/or a micro robotic surgery.

8. The power feed system according to claim 7, wherein in a case where the implant electronic device comprises a pair of light emitting diodes, one of the light emitting diodes emits light by a current flowing from the second electrode to the first electrode, and the other light emitting diode emits light by a current flowing from the first electrode to the second electrode, and
the pair of light emitting diodes are arranged respectively on a front surface side and a rear surface side of a substrate.

9. The power feed system according to claim 1, further comprising:
an engaging part that engages with a conductive holding member inserted into a tissue in the living body, wherein
the engaging part comprises a flexible conductive metal body that is deformable by compression into an elongate shape such that the same direction as a longitudinal direction of the electronic device coincides with a longitudinal direction of the engaging part.

10. A power feed system comprising:
a pair of electrodes that are stuck onto a surface of a living body;
an electronic device that includes a first electrode and a second electrode, the first electrode and the second electrode being fixed to respective positions having different electric potentials in the living body; and
a power source that applies a high frequency alternating voltage between the pair of electrodes, wherein
the power source applies a high frequency signal of 100 kHz to 4 MHz.

11. A power feed system comprising:
a pair of electrodes that are stuck onto a surface of a living body;
an electronic device that includes a first electrode and a second electrode, the first electrode and the second electrode being fixed to respective positions having different electric potentials in the living body;
a power source that applies a high frequency alternating voltage between the pair of electrodes;
a resonance circuit having at least one stage or more, which is composed of a coil and a capacitor and is configured to satisfy $f=1/(2\pi\sqrt{(LC)})$, where f is a frequency of the high frequency alternating voltage applied between the pair of electrodes, L is a self-inductance of the coil, and C is a capacitance of the capacitor; and
a booster rectifier circuit having at least one stage or more, which has two capacitors and two diodes connected in a ladder shape and converts the high frequency alternating voltage into a direct voltage, wherein
the number of stages of the booster rectifier circuit is determined according to the magnitude of parasitic components of the coil, the capacitor, and the diode.

12. A power feed system comprising:
an implant electronic device that is configured to be disposed within a living body;
a pair of surface electrodes that, when the implant electronic device is within the living body, are configured to come into contact with a surface of the living body;
a power source that, when the implant electronic device is within the living body, is configured to apply a high frequency alternating voltage between the surface electrodes to supply electric power from outside of the living body to the implant electronic device within the living body while remaining outside the living body;

a resonance circuit having at least one stage or more, which is composed of a coil and a capacitor and is configured to satisfy $f=1/(2\pi\sqrt{(LC)})$, where f is a frequency of the high frequency alternating voltage applied between the pair of electrodes, L is a self-inductance of the coil, and C is a capacitance of the capacitor; and a booster rectifier circuit having at least one stage or more, which has two capacitors and two diodes connected in a ladder shape and converts the high frequency alternating voltage into a direct voltage, wherein the number of stages of the booster rectifier circuit is determined according to the magnitude of parasitic components of the coil, the capacitor, and the diode;

wherein the implant electronic device comprises a first electrode and a second electrode, the first electrode and the second electrode being fixed to respective positions having different electric potentials in the living body.

* * * * *